(12) United States Patent
Watanabe et al.

(10) Patent No.: US 8,771,233 B2
(45) Date of Patent: Jul. 8, 2014

(54) MEDICATION ADMINISTERING DEVICE

(76) Inventors: Atsushi Watanabe, Ehime (JP); Seiji Kikuchi, Ehime (JP); Tsuguhiro Kondo, Ehime (JP)

( * ) Notice: Subject to any disclaimer, the term of this patent is extended or adjusted under 35 U.S.C. 154(b) by 84 days.

(21) Appl. No.: 13/133,229

(22) PCT Filed: Oct. 20, 2009

(86) PCT No.: PCT/JP2009/005499
§ 371 (c)(1),
(2), (4) Date: Jun. 7, 2011

(87) PCT Pub. No.: WO2010/070799
PCT Pub. Date: Jun. 24, 2010

(65) Prior Publication Data
US 2011/0238017 A1    Sep. 29, 2011

(30) Foreign Application Priority Data
Dec. 16, 2008 (JP) ................. 2008-320056

(51) Int. Cl.
*A61M 5/00* (2006.01)

(52) U.S. Cl.
USPC ....................................... 604/189

(58) Field of Classification Search
CPC ........... A61M 2205/06; A61M 2205/6081; A61M 2205/6063; A61M 2205/6036; G06F 19/3468; A61J 2205/20; A61J 2205/30
USPC ........................ 221/2, 7; 604/189
See application file for complete search history.

(56) References Cited

U.S. PATENT DOCUMENTS

| | | | |
|---|---|---|---|
| 5,468,224 A * | 11/1995 | Souryal ..................... | 604/506 |
| 6,221,051 B1 | 4/2001 | Hjertman et al. | |
| 6,585,698 B1 | 7/2003 | Packman et al. | |
| 7,164,133 B2 * | 1/2007 | Hjertman et al. ........ | 250/339.11 |
| 2002/0058928 A1 * | 5/2002 | Antonio, II ............... | 604/523 |
| 2003/0109835 A1 | 6/2003 | Woolston et al. | |

(Continued)

FOREIGN PATENT DOCUMENTS

| | | |
|---|---|---|
| CN | 1505534 A | 6/2004 |
| CN | 101010112 A | 8/2007 |

(Continued)

OTHER PUBLICATIONS

International Search Report for PCT/JP2009/005499 dated Feb. 2, 2010.

(Continued)

*Primary Examiner* — Aarti B Berdichevsky
*Assistant Examiner* — Bradley Osinski
(74) *Attorney, Agent, or Firm* — Pearne & Gordon LLP

(57) ABSTRACT

A medication administering device for automatically identifying a medication syringe and administering a correct medication. A microprocessor (20) of the medication administering device (1) identifies the color of a medication or a medication syringe on the basis of a reference value, determines the adequateness of the medication, and indicates the result of the determination by means of an LCD (10) or the like to the user. In step S4, the microprocessor (20) determines whether or not color data received from a color detecting unit (13) is within a reference value range. If the color data is within the reference value range, the microprocessor proceeds to step S5, otherwise proceeds to step S6. In step S6, the microprocessor (20) issues a message to the effect that the user needs to check the medication.

22 Claims, 15 Drawing Sheets

(56) References Cited

U.S. PATENT DOCUMENTS

| | | |
|---|---|---|
| 2003/0126598 A1 | 7/2003 | Agnihotri et al. |
| 2004/0064095 A1 | 4/2004 | Vitello |
| 2005/0029277 A1* | 2/2005 | Tachibana .................. 221/9 |
| 2005/0229931 A1 | 10/2005 | Denyer et al. |
| 2006/0206066 A1 | 9/2006 | Ferek-Petric |
| 2006/0224128 A1 | 10/2006 | Lurvey et al. |
| 2008/0200747 A1 | 8/2008 | Wagner et al. |
| 2008/0314978 A1 | 12/2008 | Fedorko et al. |
| 2009/0149744 A1* | 6/2009 | Nemoto et al. ............ 600/432 |
| 2009/0216194 A1 | 8/2009 | Pedersen et al. |

FOREIGN PATENT DOCUMENTS

| | | |
|---|---|---|
| CN | 101098723 A | 1/2008 |
| CN | 101184518 A | 5/2008 |
| JP | 2000-513967 A | 10/2000 |
| JP | 2001-017542 A | 1/2001 |
| JP | 3151230 B2 | 1/2001 |
| JP | 2001-170176 A | 6/2001 |
| JP | 2003-521977 A | 7/2003 |
| JP | 2004-261274 A | 9/2004 |
| JP | 2004-298550 A | 10/2004 |
| JP | 2005-511155 A | 4/2005 |
| JP | 2005-287676 A | 10/2005 |
| JP | 2008-532644 A | 8/2008 |
| JP | 2008-537491 A | 9/2008 |
| WO | 99/47062 A1 | 9/1999 |
| WO | 02/058767 A1 | 8/2002 |
| WO | 03024385 A1 | 3/2003 |
| WO | 2006054651 A1 | 5/2006 |
| WO | 2006/084464 A1 | 8/2006 |
| WO | 2007114446 A1 | 10/2007 |
| WO | 2008019494 A1 | 2/2008 |
| WO | 2008/091623 A2 | 7/2008 |
| WO | 01/74422 A1 | 10/2011 |

OTHER PUBLICATIONS

English Translation for Chinese Search Report for Application No. 200980150567.4 dated Aug. 14, 2013.

Extended European Search Report for Application No. 09833109.3-1662/2359881 dated Mar. 19, 2013.

* cited by examiner

MEDICATION ADMINISTERING DEVICE

TECHNICAL FIELD

The present invention relates to a drug administration apparatus that has a formulation syringe containing formulation mounted inside and can administer drug to a living body and so forth, and more particularly, relates to a drug administration apparatus that automatically identifies the mounted formulation.

BACKGROUND ART

When administering drug solution from a formulation syringe to a test subject, the operator prepares a formulation syringe containing appropriate drug solution. A drug administration apparatus administers drug solution from a formulation syringe to a test subject by moving a piston member relative to a cylinder member by means of an injecting mechanism, in response to predetermined operation.

Conventionally, a drug injection system including a drug administration apparatus has come into practical use, in which a barcode reader provided in the drug administration apparatus reads the barcode printed on a formulation packing material, or the barcode affixed to a formulation syringe, and the result is displayed on a display section, so that the operator can easily and reliably check the formulation (e.g. Patent Literature 1).

FIGS. 1A and B each show a configuration of a conventional drug administration apparatus, and FIG. 2 shows a display example of the barcode label on the conventional drug administration apparatus.

As shown in FIGS. 1A and B and FIG. 2, a drug injection system has drug solution injecting device 100 and drug solution syringe 200.

Drug solution injecting device 100 is provided with touch panel 105, barcode reader 108 and injection head 110. Two concave parts 112, as a syringe holding mechanism, are formed in injection head 110, and cylinder members 201 in respective drug solution syringes 200 are removably held in these concave parts 112 separately.

Drug solution syringe 200 is composed of cylinder member 201 and piston member 202, and piston member 202 is slidably inserted in cylinder member 201. Cylinder member 201 is filled with drug solution and capped with sealing cap 203, and then sealed with packing material 204 wholly.

Identification data 205 on drug solution is recoded on at least one of the packing material, cylinder member and piston member in drug solution syringe 200, and the drug administration apparatus stores drug solution data per identification data 205. In the drug administration apparatus, barcode reader 108 retrieves read drug solution data, and display section 108 displays it, and therefore, the operator can easily and reliably check various data about drug solution to be injected into the test subject.

CITATION LIST

Patent Literature

PTL 1
Japanese Patent Application Laid-Open No. 2004-298550

SUMMARY OF INVENTION

Technical Problem

However, this conventional formulation injection system identifies formulation by barcode, and therefore has a problem that it is difficult for the user to identify formulation only by looking at a formulation syringe.

In addition, in the above-described case, identifying formulation by the barcode and mounting a formulation syringe in the drug solution injecting device are not performed at the same time, and therefore, if the user mounts a formulation syringe different from one identified by the barcode by mistake, there is a risk of administrating wrong drug. Moreover, there is a problem that it is necessary to provide a barcode reader in the drug administration apparatus side, so that the size of the apparatus increases, and therefore mobility deteriorates and the cost increases.

In view of the above-described problems, it is therefore an object of the present invention to provide a drug administration apparatus that can administer correct drug by automatically identifying formulation syringes.

Solution to Problem

The drug administration apparatus according to the present invention that has a formulation syringe containing formulation mounted inside and administers drug to a living body adopts a configuration to include: an identification section that identifies formulation loaded in the formulation syringe, or the formulation syringe containing the formulation; and a reporting section that reports a result of identification by the identification section.

Advantageous Effects of Invention

According to the present invention, it is possible to administer correct drug by automatically identifying formulation loaded into a formulation syringe or a formulation syringe containing formulation and reporting the result of the identification.

In addition, it is possible to realize a compact drug administration apparatus that can easily and reliably identify formulation without damaging convenience for the user, and it is possible to provide a safe and secure drug administration apparatus that prevents wrong drug from being administered.

DESCRIPTION OF EMBODIMENTS

Now, embodiments of the present invention will be described in detail with reference to the accompanying drawings.

Embodiment 1

Figure 1A:
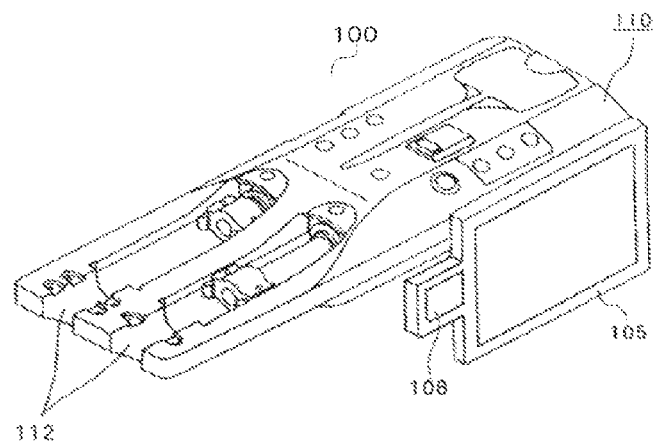
FIGS. 1A and B each show a configuration of a conventional drug administration apparatus.
Figure 1B:
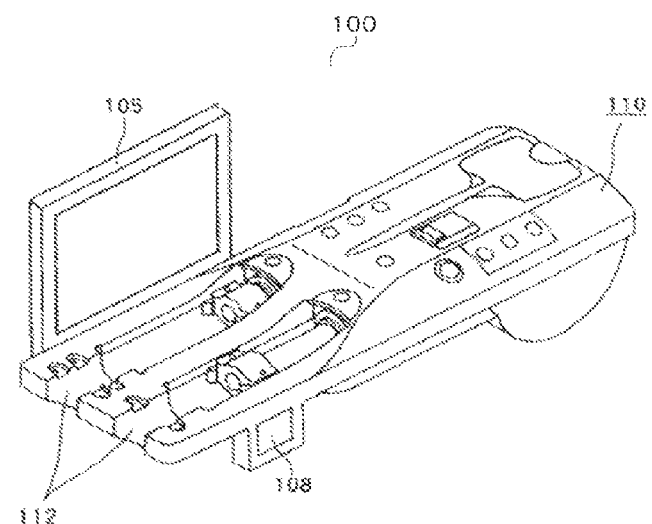
Figure 2:
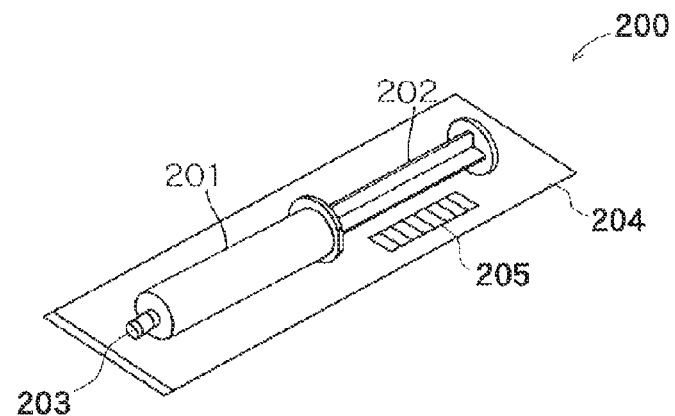
FIG. 2 shows a display example of the barcode label on the conventional drug administration apparatus.
Figure 3:
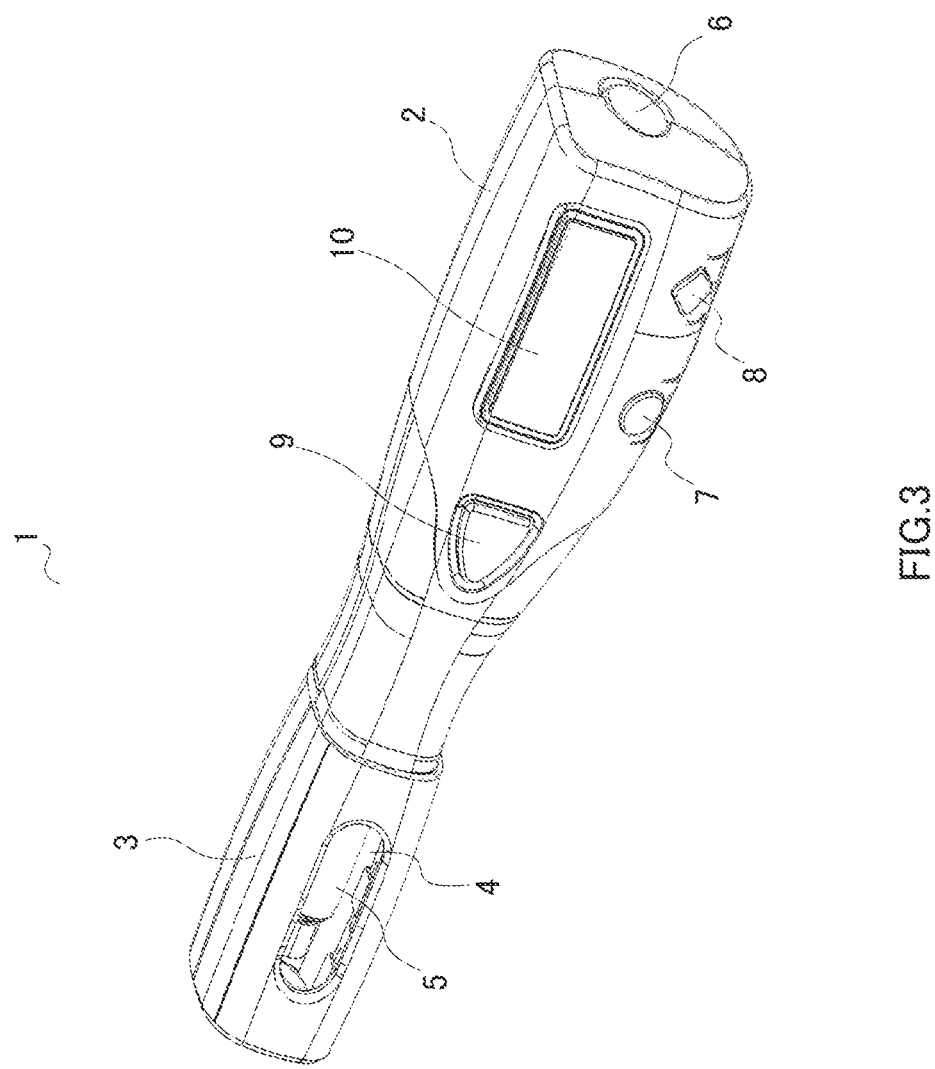
FIG. 3 is an overall perspective view showing a drug administration apparatus according to Embodiment 1 of the present invention.

FIG. 3 is an overall perspective view showing a drug administration apparatus according to Embodiment 1 of the present invention.

As shown in FIG. 3, drug administration apparatus 1 is configured to include housing 2, tip cap 3, check window 4, syringe cover 5, detecting protrusion 5b (see FIG. 4), power supply button 6, air-bleeding button 7, completion button 8, drug administration button 9 and LCD (liquid crystal display) 10, which is a display means.

Drug administration apparatus 1 is covered with housing 2, which is the exterior of the apparatus body.

Tip cap 3 is removably mounted to one end of housing 2 and, if necessary, is mounted or removed when formulation syringe 11 is mounted or removed, and an injection needle for injecting drug solution is mounted or removed.

Tip cap 3 has check window 4 for checking the inside, and therefore, it is possible to visually check the presence or absence and the type of formulation syringe 11 (see FIG. 4), the amount of formulation and so forth through syringe cover 5 made of a transparent member.

In addition, tip cap 3 serves to cover an injection needle for drug administration in order not to expose the injection needle, and, at the time of drug administration, skin is made contact tip cap 3 and punctured with an injection needle for drug administration from a top opening part in tip cap 3 to administer drug. Tip cap 3 secures safety in operation by covering a member having a sharply pointed tip such as an injection needle.

Check window 24 is a window for checking the inside, which visually checks the presence or absence and the type of formulation syringe 11 (see FIG. 4), and the amount of formulation and so forth through syringe cover 5 made of a transparent member. Check window 4 may be made of, for example, a transparent or semi-transparent member, or may be an opening physically clipped off as long as check window 4 allows the inside to be visually checked.

Power supply button 6 turns on and off the power supply of drug administration apparatus 1. By this means, drug administration apparatus 1 is activated.

Air-bleeding button 7 is used when air in formulation syringe 11 (see FIG. 4) is bled. In case formulation syringe 11 or an injection needle (hollow needle whose inside is hollow) for drug administration contains air, this air-bleeding button 7 removes the inside air from formulation syringe 11 and so forth.

Completion button 8 allows the step to move the next step after air-bleeding operation, or when necessary operation, including checking various displays and so forth, is completed.

After completing preparation for drug administration, drug administration button 9 is pushed at the time of drug administration.

LCD 10 displays various necessary information including a battery level, air-bleeding operation and so forth.

Figure 4:
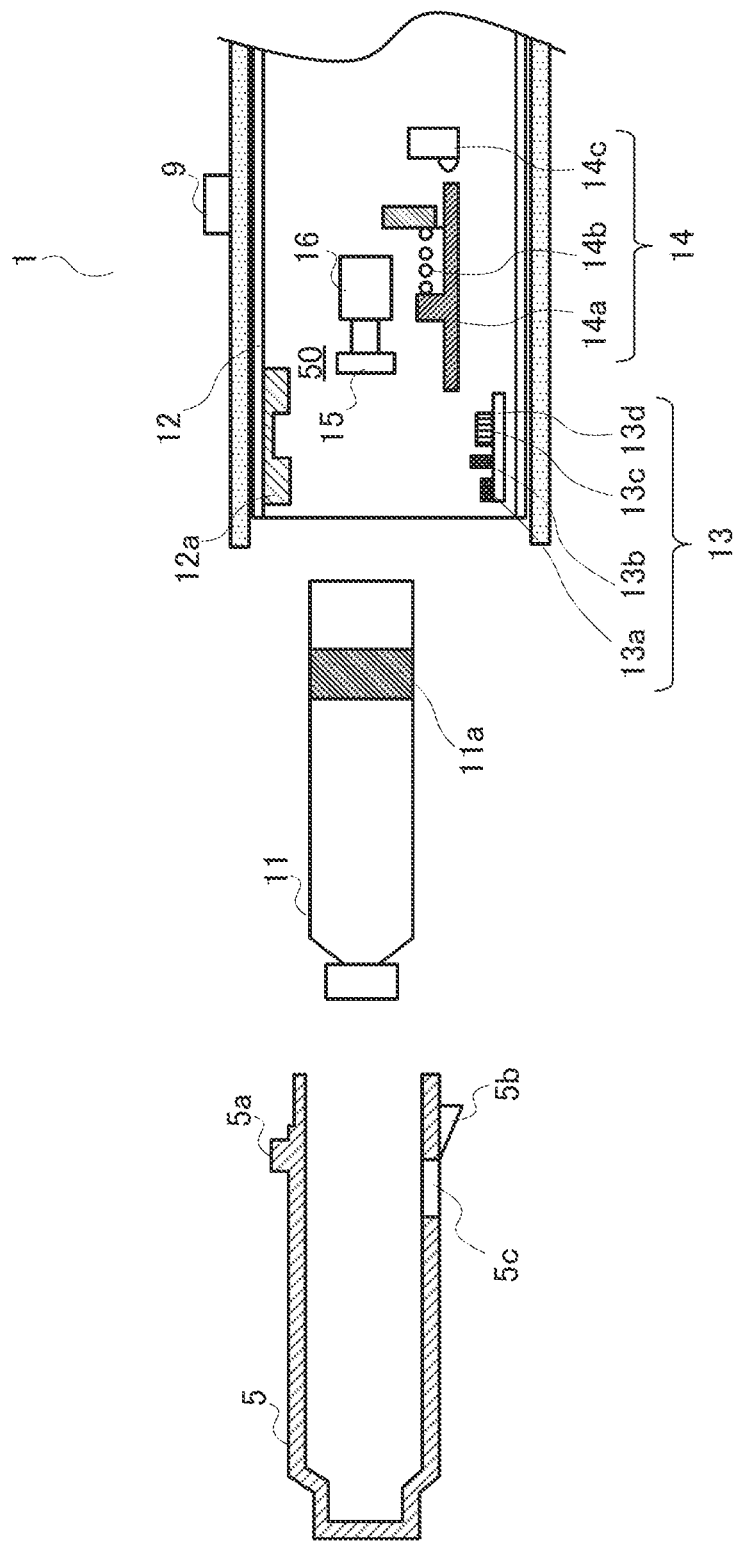
FIG. 4 is a cross sectional view showing the internal state before a formulation syringe is mounted in a syringe holder in the drug administration apparatus according to Embodiment 1.
Figure 5:
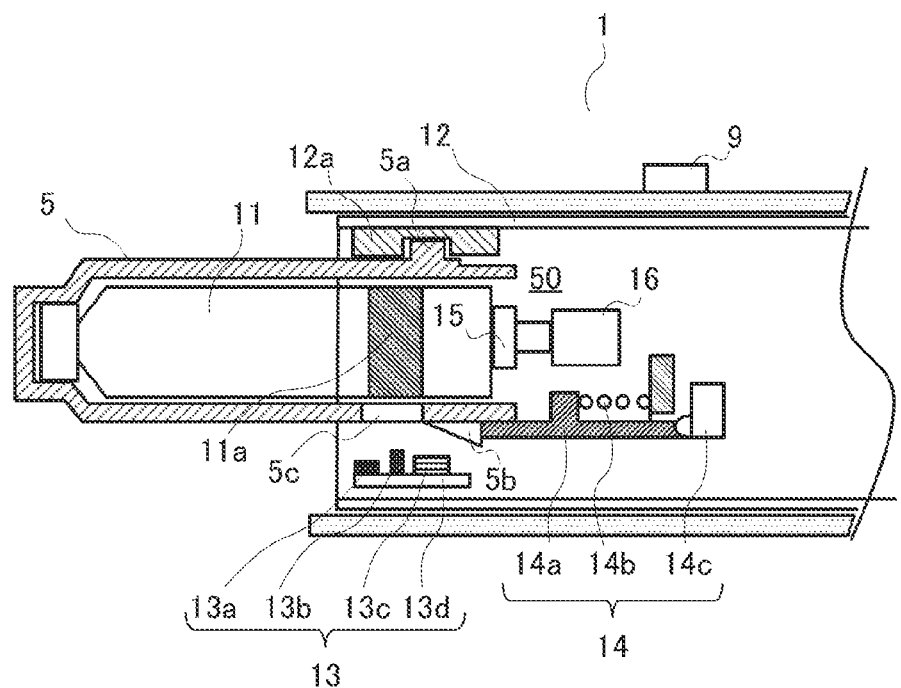
FIG. 5 is a cross sectional view showing the internal state after a formulation syringe is mounted in a syringe holder in the drug administration apparatus according to Embodiment 1.

FIGS. 4 and 5 are cross sectional views showing states before and after formulation syringe 11 is mounted in drug administration apparatus 1. FIG. 4 is a cross sectional view showing the internal state before formulation syringe 11 is mounted in syringe holder 50, which is a mounting section in the drug administration apparatus 1 side. FIG. 5 is a cross sectional view showing the internal state after formulation syringe 11 is mounted in syringe holder 50.

Syringe holder 50 is a mounting section that mounts formulation syringe 11 in drug administration apparatus 1 body, and includes piston case 12, attaching and removing groove 12a, piston 15 and so forth. Syringe holder 50 restricts formulation syringe 11 from inserting in syringe holder 50 in the direction of the central axis of formulation syringe 11 and holds it by making the bottom of formulation syringe 11 contact piston 15, and restricts formulation syringe 11 from shifting in the direction of the outer surface of formulation syringe 11 and holds it by fitting formulation syringe 11 into piston case 12 and attaching and removing groove 12a.

In a state before syringe cover 5 is mounted as shown in FIG. 4, syringe cover 5 is removed from drug administration apparatus 1, and, after formulation syringe 11 is inserted in drug administration apparatus 1, syringe cover 5 is mounted, and then fitted into piston case 12 placed in housing 2. As shown in FIG. 4, syringe cover 5 has attaching and removing protrusion 5a, detecting protrusion 5b and opening 5c.

As shown in FIG. 5, in a state after syringe cover 5 is mounted in drug administration apparatus 1, attaching and removing protrusion 5a is fitted into attaching and removing groove 12a formed in the inner surface of piston case 12 provided in housing 2.

Detecting protrusion 5b is provided to push one end of syringe cover detecting lever 14a formed in housing 2.

Formulation syringe 11 has label 11a used for color detection.

Piston case 12 is a member having an approximately cylindrical shape and provided along the inner surface of housing 2. Drug administration button 9 is provided in the outer surface side of piston case 12, and detecting section 13, which is an identification means, syringe cover detecting section 14, piston 15 and piston driving motor 16 are provided in piston case 12.

Drug administration button 9 is provided on the side surface of drug administration apparatus 1 and pressed at the time of drug administration.

Piston 15 moves forward and pushes formulation toward the direction of drug administration (the left in FIG. 5).

Syringe cover detecting section 14 has syringe cover detecting lever 14a, syringe cover detecting lever spring 14b and syringe cover detecting switch 14c. When syringe cover 5 is inserted in piston case 12, syringe cover detecting lever 14a is pushed by detecting protrusion 5b provided on syringe cover 5 and moves against the spring force of syringe cover detecting lever spring 14b to press syringe cover detecting switch 14c. By this means, it is possible to detect syringe cover 5 being mounted in piston case 12.

Piston driving motor 16 moves piston 15 forward and backward (expands and contracts piston 15) in the direction of drug administration by rotating in a desired direction.

Figure 6:
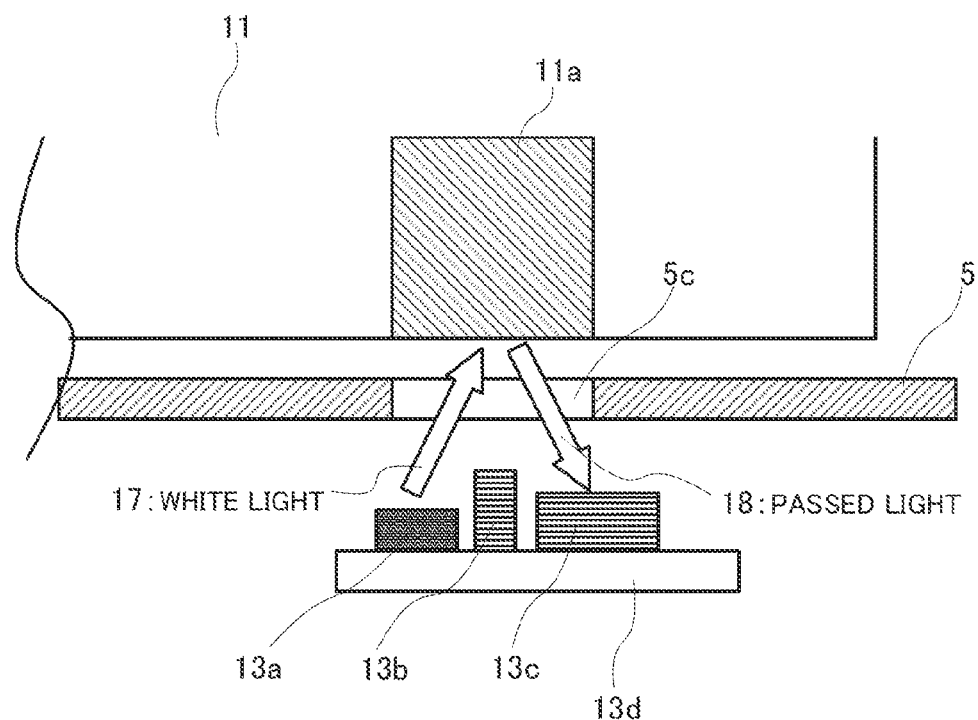
FIG. 6 is an enlarged cross sectional view showing primary parts nearby a color detecting section in the drug administration apparatus according to Embodiment 1.

FIG. 6 is an enlarged view showing parts nearby color detecting section, which is an example of an identification means.

As shown in FIG. 6, color detecting section 13 has LED 13a, light blocking wall 13b, color sensor 13c and printed substrate 13d.

In color detecting section 13, when white light 17 outputted from LED 13a and containing RGB components passes through opening 5c and hits label 11a affixed to formulation syringe 11, white light 17 is converted into reflected light 18 having the same color component as label 11a, and color sensor 13c receives reflected light 18 which passes through opening 5c and arrives at color sensor 13c, performs digital-conversion on reflected light 18 and outputs the result to microprocessor 20 (see FIG. 7), and therefore, it is possible to accomplish color detection. Light blocking wall 13b serves to prevent white light 17 of LED 13a from directly entering color sensor 13c and allows accurate color detection of label 11a affixed to a formulation syringe.

Figure 7:
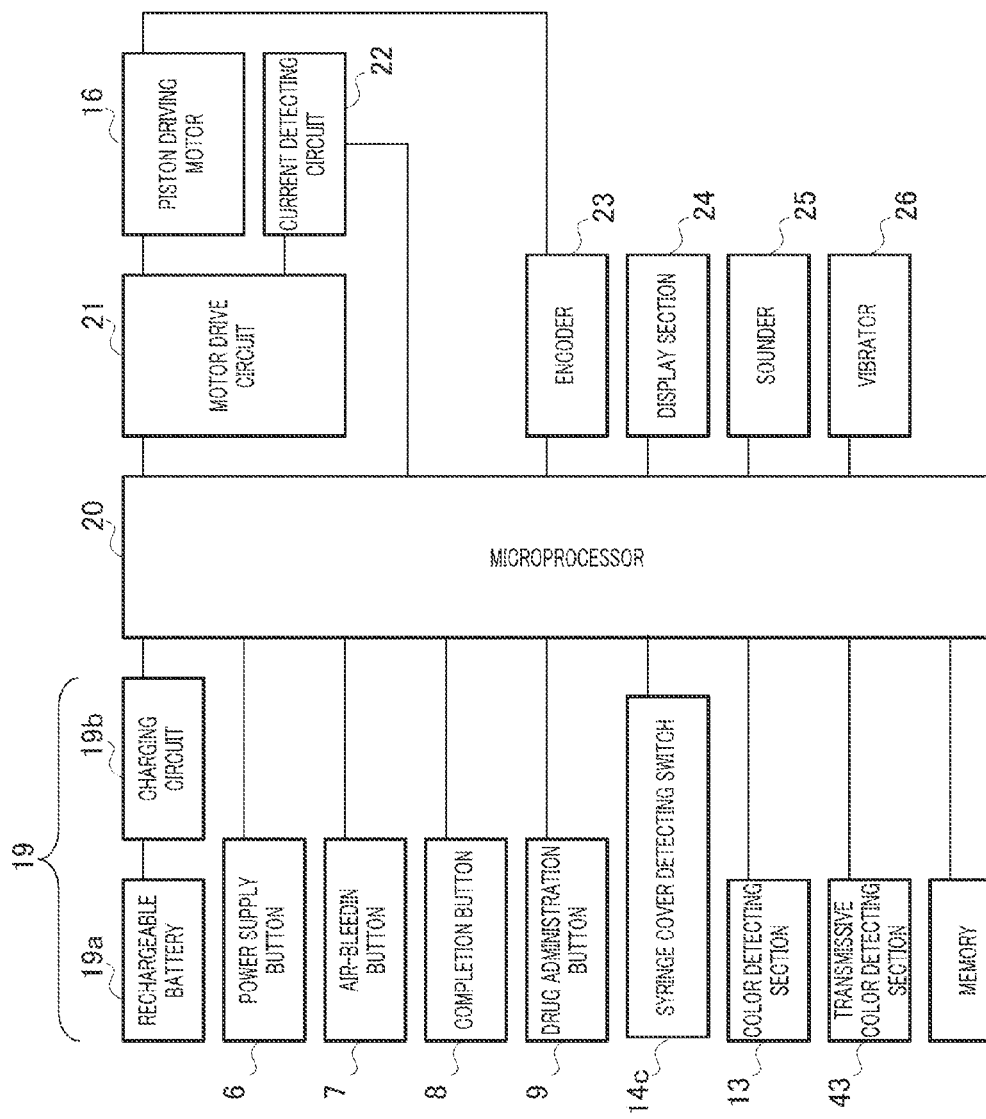
FIG. 7 is a block diagram showing the electrical circuit of the drug administration apparatus according to Embodiment 1.

FIG. 7 is a block diagram showing the electrical circuit of drug administration apparatus 1 and its nearby parts.

As shown in FIG. 7, in drug administration apparatus 1, power supply button 6, air-bleeding button 7, completion button 8, drug administration button 9, color detecting section 13, syringe cover detecting switch 14c and piston driving motor 16 are electrically connected to microprocessor 20, which is a control section. In addition, drug administration apparatus 1 is configured to include power supply section 19, which is the power supply of the apparatus, motor drive circuit 21, current detecting circuit 22, encoder 23, display section 24 (LCD 10), sounder 25 and vibrator 26.

Power supply button 6 is used to switch the power supply between on and off in drug administration apparatus 1. By turning on the power supply, drug administration apparatus 1 is activated.

Air-bleeding button 7 is used to perform air-bleeding operation, which is generally performed as advance preparation before drug administration.

Completion button 8 is pressed at the time necessary operation is completed to move the step to the next step.

Drug administration button 9 is used when it is desired to start drug administration operation.

Power supply section 19 represents the power supply part of drug administration apparatus 1. Power supply section 19 has a mobility-focused configuration and is composed of rechargeable battery 19a and charging circuit 19b. Here, power supply section 19 can operate using a primary battery. Nickel metal hydride battery and a lithium-ion battery may be used as rechargeable battery 19.

Display section 24, sounder 25 and vibrator 26 are used as means for reporting to the user. Display section 24 refers to LCD 10, an LED, organic electro-luminescence and so forth, and is used to visually check the current operation state, warning display and so forth.

An optical reporting method using a display LED and so forth can be realized by illuminating, flashing and so forth. In addition, when a multicolor type display LED and so forth is used, it is possible to visually report the degree of importance or urgency of the reported content by switching RGB components and illuminating or flashing any color based on the ratio between colors. Therefore, it is useful for people with impaired hearing.

In addition, the above-described display LED may be provided separately from LCD 10. Display section 24 may be arranged nearby a mounting section to mount formulation syringe 11 in drug administration apparatus 1.

Sounder 25 is used to perform auditory reporting by warning sound, the sound during drug administration, audio output at the time of starting and ending electrical charging, announce of operation by sound, and so forth, according to audio signals from microprocessor 20. Therefore, it is useful for people with impaired sight.

Vibrator 26 reports warning and so forth by vibration. Vibrator 26 reports an abnormal state and so forth to the user by vibration instead of or as well as a warning sound or voice, and therefore can effectively and reliably inform the state of a drug administration apparatus and so forth.

Microprocessor 20 controls the overall operation of the apparatus and also controls operation of the apparatus corresponding to each of various buttons 6 to 9, according to electrical signals transmitted from these buttons 6 to 9.

Particularly, microprocessor 20 controls operation of drug administration. To be more specific, when drug administration button 9 is pushed, microprocessor 20 checks syringe cover detecting switch 14c and color detecting section 13 to check whether or not formulation syringe 11 is normally mounted. After checking whether or not formulation syringe 11 is normally mounted, microprocessor 20 transmits an electrical signal to motor drive circuit 21 to operate piston driving motor 16. When piston driving motor 16 rotates, piston 15 (see FIG. 4) mechanically connected to piston driving motor 16 moves forward, and therefore drug is administered from formulation syringe 11 into the living body. The dosage of drug is determined and managed by counting output signals (pulse signals) from encoder 23 connected to piston driving motor 16.

In addition, microprocessor 20 has a function as an identification means to identify a formulation syringe by executing a program described later with reference to FIG. 8 and FIG. 9. Moreover, microprocessor 20 can administer drug into a living body by automatically controlling the dosage of drug by motor drive circuit 21, based on information about a preset dosage of drug. That is, microprocessor 20 also has a drug dosage control section. In addition, microprocessor 20 further has a drug administration information setting section that sets information about drug administration such as the dosage of drug. A reference value to identify color of formulation or a formulation syringe is preset, and information about drug administration including the reference value and the dosage of drug is stored in a memory.

When abnormal load is applied to piston driving motor 16 (when an injection needle cannot be mounted or clogs), a current value varies more greatly than usual, and current detecting circuit 22 detects the abnormal current value and transmits an electrical signal to microprocessor 20. Upon receiving the electrical signal, microprocessor 20 determines that there is something wrong and stops the drug administration operation, and then, reports the abnormality to the user by displaying an error and so forth on LCD 10, flashing a display LED, outputting a warning sound by sounder 25 and vibrating vibrator 26.

Syringe cover detecting switch 14c constituting syringe detecting section 14 is equivalent to a formulation syringe detecting section that detects whether or not formulation or formulation syringe 11 has been mounted in drug administration apparatus 1 and detects whether a formulation syringe is correctly mounted at the time of replacing a formulation syringe.

Now, operation of drug administration apparatus 1 configured as described above, will be explained.

First, operation of formulation syringe 11 at the time of replacement will be described.

Figure 8:
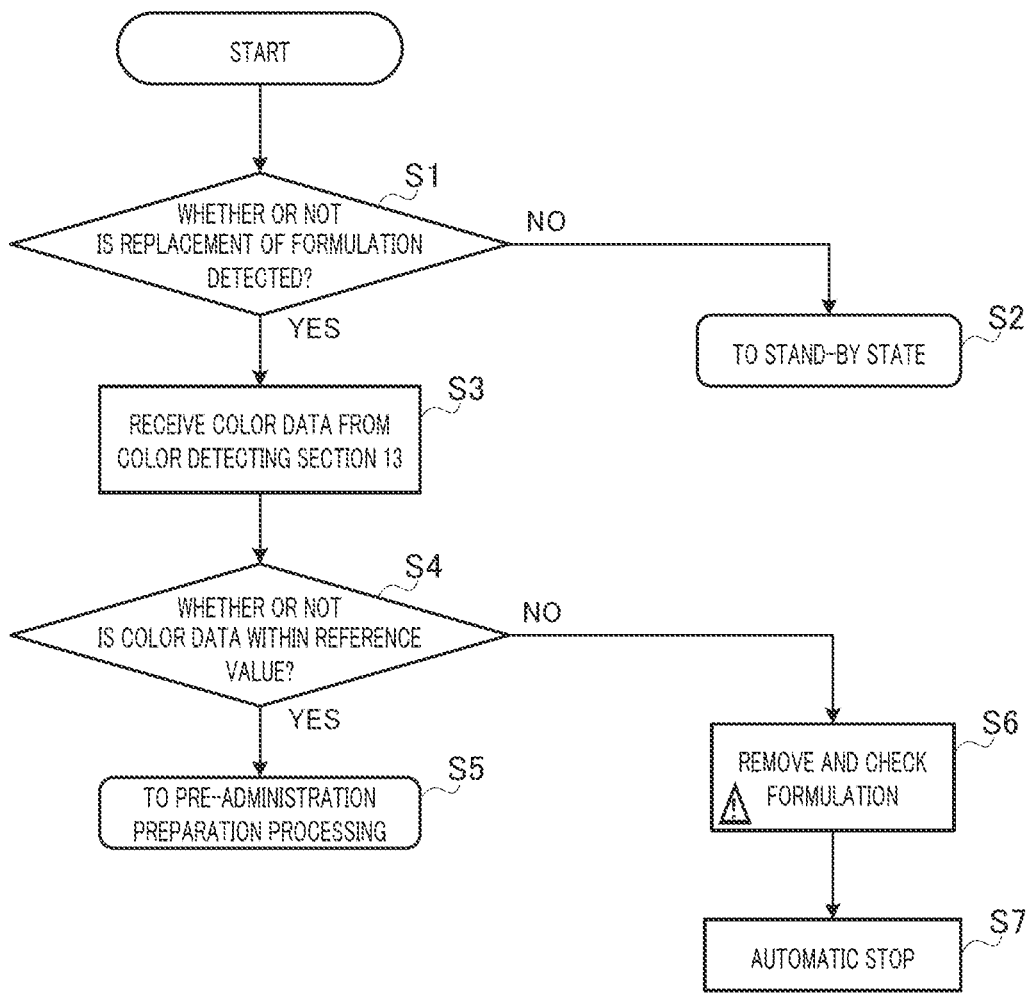
FIG. 8 is a flowchart showing operation of formulation identification when a formulation syringe is replaced in the drug administration apparatus according to Embodiment 1.

FIG. 8 is a flowchart showing operation of formulation identification at the time of replacing formulation syringe 11, and this flow is executed by microprocessor 20. In the figure, S represents each step in the operation flow.

In step S1, microprocessor 20 checks whether formulation syringe 11 has been correctly mounted in drug administration apparatus 1 using syringe cover detecting switch 14c and so forth. When formulation syringe 11 has not been mounted, the step moves to a stand-by mode in step S2.

When formulation syringe 11 has been mounted, microprocessor 20 receives color data from color detecting section 13 in step S3.

In step S4, microprocessor 20 determines whether or not the color data received from color detecting section 13 is within the reference value. If the color data is within the reference value, the step moves to step S5, and, on the other hand, when the color data is out of the reference value, the step moves to step S6.

In step S5, assume that a correct formulation syringe has been mounted, microprocessor 20 moves the step to pre-administration preparation processing including air-bleeding operation.

In step S6, assume that a wrong formulation syringe has been mounted, microprocessor 20 issues a message to warn and report that the formulation should be checked. To be more specific, in order to inform the user about that wrong drug is likely to be administered, microprocessor 20 displays a warning such as a message indicating "! remove and check formulation" on LCD 10, which is a display means. In addition, microprocessor 20 makes sounder 25 issue a warning sound and also makes vibrator 26 vibrate. In addition, reporting may be made by flashing a display LED. Moreover, combination of these is possible.

In step S7, microprocessor 20 makes drug administration apparatus 1 automatically stop in order to prevent wrong drug from being administered. Automatically preventing wrong drug from being administered in the drug administration apparatus 1 side is greatly useful to secure the safety of the user.

In addition, operation of identifying formulation and/or a formulation syringe is also performed at the time of staring drug administration.

Figure 9:
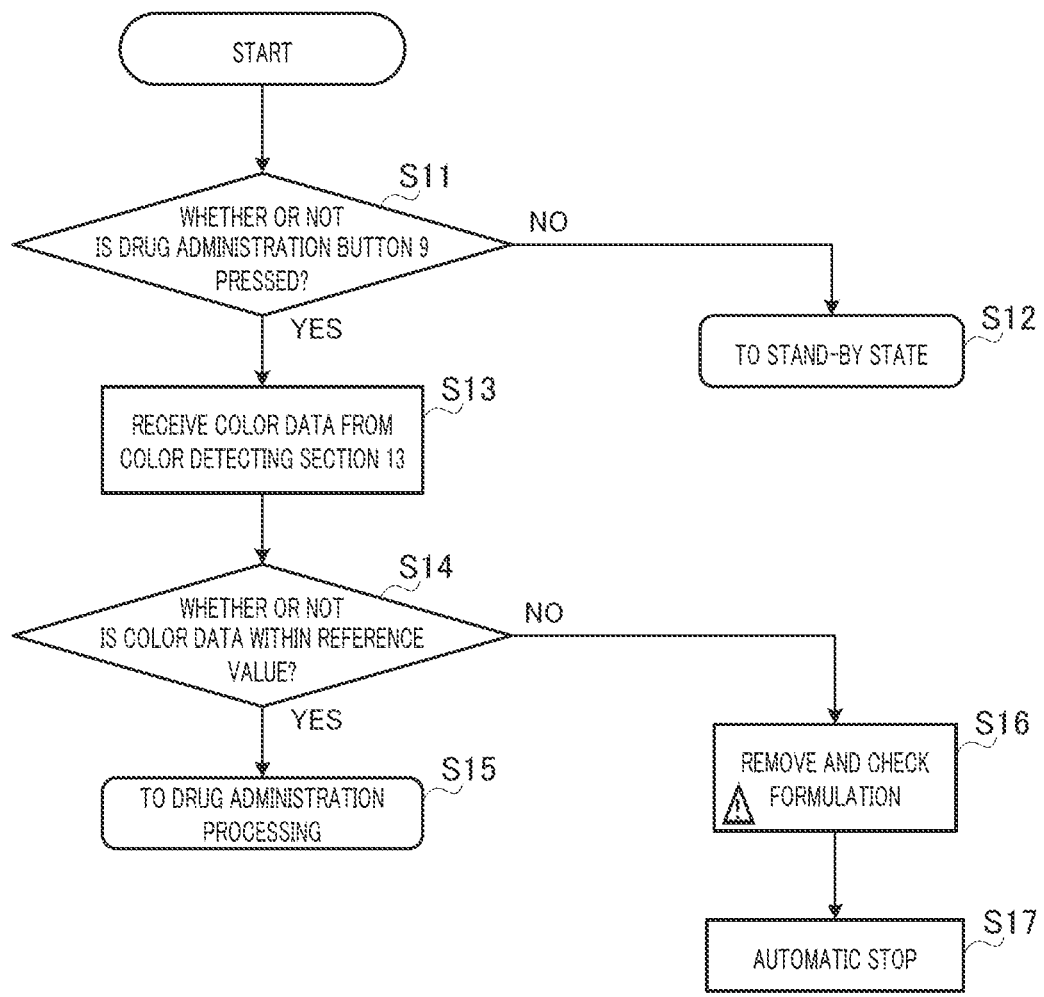
FIG. 9 is a flowchart showing operation of formulation identification when drug is administered from a formulation syringe in the drug administration apparatus according to Embodiment 1.

FIG. 9 is a flowchart showing formulation identification operation at the time of administering drug from formulation syringe 11. The basic operation is the same as the flow shown in FIG. 8.

In step S11, microprocessor 20 checks whether or not drug administration button 9 has been pressed by the user. If drug administration button 9 has not been pressed by the user, the step moves to a stand-by mode in step S12.

If drug administration button 9 has been pressed by the user, the step moves to step S13, and microprocessor 20 receives color data from color detecting section 13.

In step S14, microprocessor 20 determines whether or not the color data received from color detecting section 13 is within the reference value. If the color data is within the reference value, the step moves to step S15, and, on the other hand, if the color data is out of the reference value, the step moves to step S16.

In step S15, assuming that a correct formulation syringe is mounted, microprocessor 20 moves to drug administration processing.

In step S16, microprocessor 20 sends a message to report that formulation should be checked. To be more specific, in order to inform the user that wrong drug is likely to be administered, microprocessor 20 displays a warning indicating "! remove and check formulation" on LCD 10. In addition, microprocessor 20 makes sounder 25 issue a warning sound and also makes vibrator 26 vibrate. Moreover, microprocessor 20 may issue a warning by flashing display LED. Furthermore, combination of these is possible.

In step S17, assuming that a wrong formulation syringe is mounted, microprocessor 20 makes drug administration apparatus 1 automatically stop in order to prevent wrong drug from being administered. Automatically preventing wrong drug from being administered in the drug administration apparatus 1 side is greatly useful to secure the safety of the user.

In this way, formulation is identified at the time of starting drug administration (including just before starting drug administration), so that it is possible to reduce the risk of administering wrong drug. This processing prevents wrong drug administration.

The reason formulation is identified before drug administration is to certainly prevent wrong drug administration even if formulation identification processing has not been performed for some reason at the time of formulation replacement shown in FIG. 8. In addition, the reason formulation identification processing is performed both at the time of drug administration shown in FIG. 9 and at the time of formulation replacement shown in FIG. 8, is to improve reliability by double checking, and that it is preferable to avoid stopping administering drug at the last minute and find wrong drug in the preparation stage before administration.

Here, formulation identification processing may be performed either at the time of drug administration shown in FIG. 9 or at the time of formulation replacement shown in FIG. 8. However, from the viewpoint of reliably preventing wrong drug administration, the present embodiment is preferable in which formulation identification processing is performed both at the time of drug administration and at the time of formulation replacement.

As described above in detail, microprocessor 20 provided in drug administration apparatus 1 according to the present embodiment identifies the availability and so forth of formulation by determining the color of formulation or a formulation syringe based on the reference value, and reports the result of the identification to the user using LCD 10 and so forth, so that it is possible to automatically identify formulation syringes to administer correct drug. The user does not need work including checking a formulation syringe by the user's eyes, and therefore can check a formulation syringe without trouble. In addition, it is possible to easily and reliably identify formulation without damaging convenience for the user. Moreover, the size of the apparatus does not increase.

In addition, with the present embodiment, the syringe cover detecting means and the color detecting means shown in FIG. 4, FIG. 5 and FIG. 6 are provided to determine whether or not a formulation syringe has been mounted and it is possible to use formulation. Replacing a formulation syringe and pressing the drug administration button are necessary work for drug administration, and this work allows automatic detection of the validity of a formulation syringe. Consequently, it is possible to easily and reliably determine whether or not drug can be administered, and then, the result of the determination is reported to the user, so that the user can easily administer drug.

Moreover, although with the present embodiment, the color of formulation or formulation syringe 11 is detected by reflected light, the present invention is not limited to this, and, when formulation syringe 11 and syringe cover 5 are integrated, an identification method by coloring syringe cover 5 itself for identification is possible, and also an identification method by attaching color identification label 11a to syringe cover 5 is possible. Basically, it is possible to provide the same effect as in the present embodiment by using the same method as in the present embodiment.

Embodiment 2

Embodiment 2 is an example in which a transmissive color detecting section is applied to a color detecting means.

Figure 10:
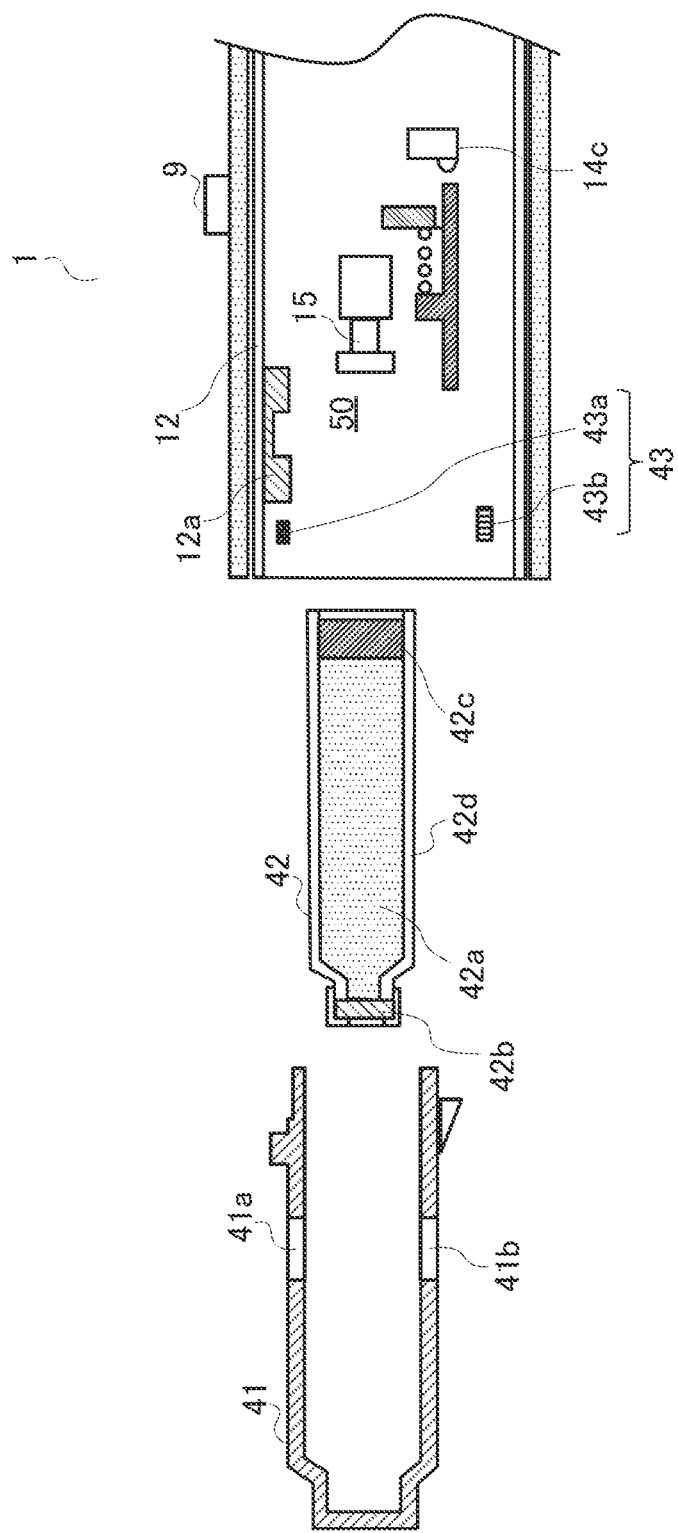
FIG. 10 is a cross sectional view showing the internal state before a formulation syringe is mounted in a syringe holder in a drug administration apparatus according to Embodiment 2 of the present invention.
Figure 11:
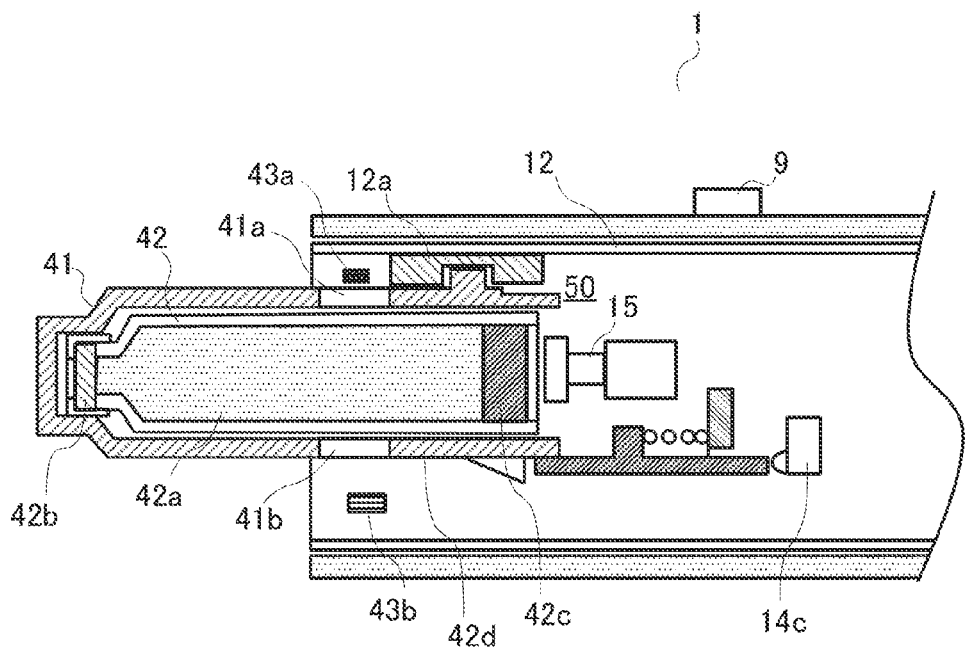
FIG. 11 is a cross sectional view showing the internal state after a formulation syringe is mounted in a syringe holder in the drug administration apparatus according to Embodiment 2.

FIG. 10 and FIG. 11 are cross sectional views showing states before and after formulation syringe 42 is mounted in drug administration apparatus 1 according to Embodiment 2 of the present invention. FIG. 10 is a cross sectional view showing the internal state before formulation syringe 42 is mounted in syringe holder 50. FIG. 11 is a cross sectional view showing the internal state in which formulation syringe 42 is mounted in syringe holder 50. The same components as in FIG. 4 and FIG. 5 are assigned the same reference numerals and overlapping descriptions will be omitted.

As shown in FIG. 10 and FIG. 11, syringe cover 41 is a transmissive color detecting means, and has first opening 41a and second opening 41b. In addition, syringe cover 41 is partly or entirely formed by a transparent member.

Formulation syringe 42 is formed as a transparent container, and has formulation 42a, first gasket 42b, second gasket 42c and container 42d.

Transmissive color detecting section 43 has LED 43a and color sensor 43b. Detailed description will be explained with reference to FIG. 12.

In a state before syringe cover 41 is mounted as shown in FIG. 10, syringe cover 41 is removed from drug administration apparatus 1, and, after formulation syringe 42 is inserted in drug administration apparatus 1, syringe cover 41 is mounted, and then fitted into piston case 12 placed in housing 2.

FIG. 11 shows a state after syringe cover 41 is mounted, where formulation syringe 42 is covered with syringe cover 41, and first opening 41a and second opening 41b in syringe cover 41 match LED 43a and color sensor 43b in transmissive color detecting section 43, respectively.

Figure 12:
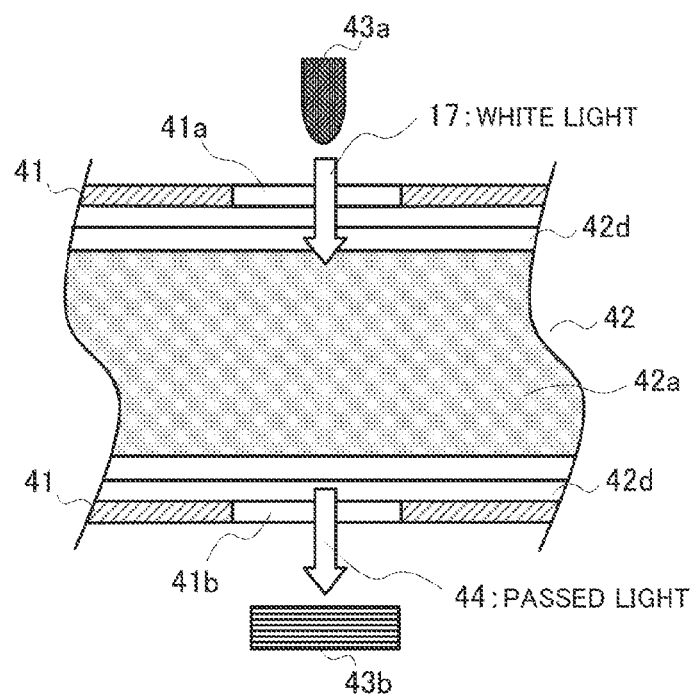
FIG. 12 is an enlarged cross sectional view showing primary parts nearby a transmissive color detecting section in the drug administration apparatus according to Embodiment 2.

FIG. 12 is an enlarged cross sectional view showing primary parts nearby the above-described transmissive color detecting section 43.

As shown in FIG. 12, transmissive color detecting section 43 has LED 43a and color sensor 43b. In transmissive color detecting section 43, white light 47 containing RGB components outputted from LED 43a passes through formulation syringe 42 to convert passed light 44, and color sensor 43b performs digital-conversion on this passed light 44 and outputs the result to microprocessor 20.

Passed light 44 passes through formulation 42a accommodated in formulation syringe 42 or container 42d, and therefore, has the same color component as formulation 42a or container 42d by filler effect. Therefore, it is possible to detect the color of formulation 42a or container 42d.

In this way, according to Embodiment 2, like Embodiment 1, the color of formulation or a formulation container is automatically identified, so that the user does not need work including checking a formulation syringe by the user's eyes, and therefore can check whether or not the formulation is correct without trouble. It is possible to easily and reliably determine whether or not the formulation is correct based on the color of the formulation itself without damaging convenience for the user, so that it is possible to improve the safety and also operability.

In addition, with Embodiment 2, it is possible to identify the color of formulation itself, and this provides a specific effect that can automatically identify formulation even if blood flows back from the living body side to the formulation syringe side, or event if the color of formulation changes in a poor state of preservation.

Moreover, it was found that even if different types of formulation having the same color were used, it was possible to automatically identify formulation by varying the color of a container for each kind of formulation and identifying the color of each container.

Embodiment 3

Embodiment 3 is an example in which the characteristic of the reflective color detecting section according to Embodiment 1 is exploited and a plurality of color detecting means are further provided.

Figure 13:
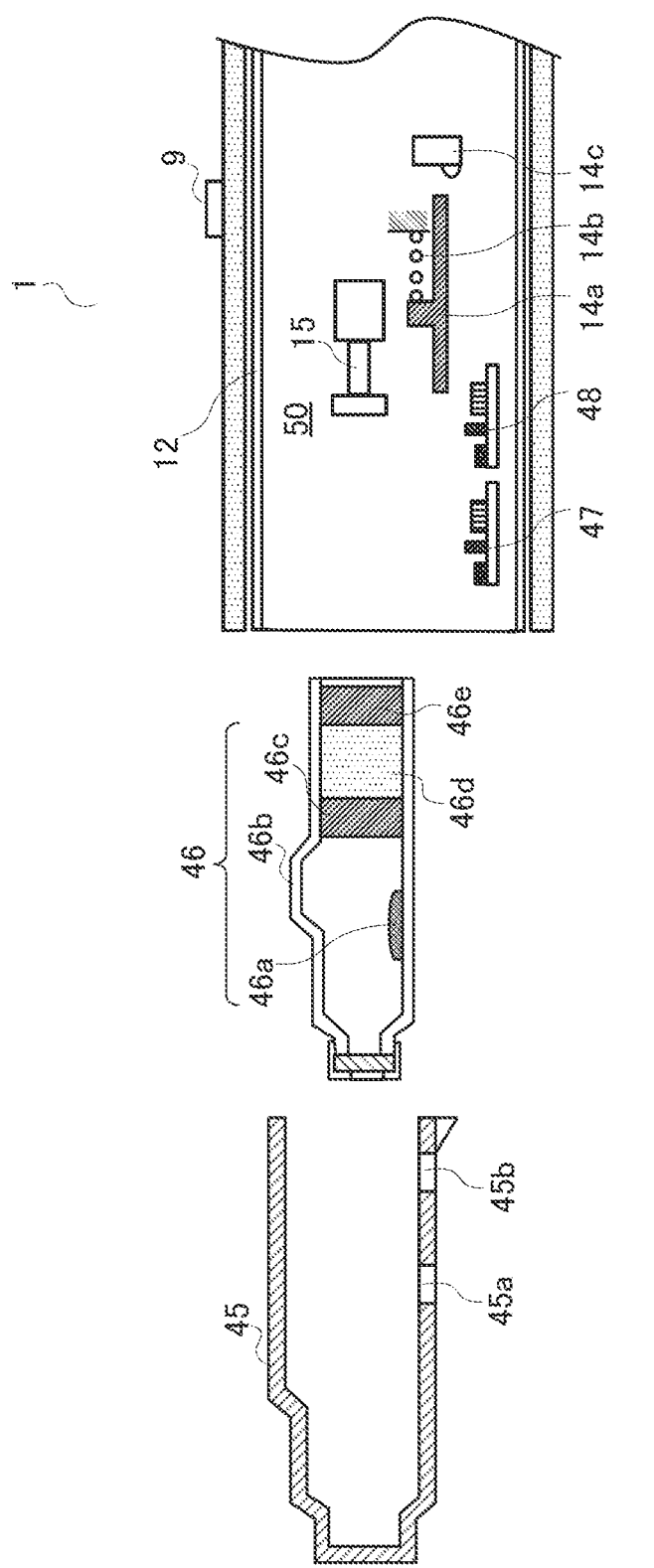
FIG. 13 is a cross sectional view showing the internal state before a formulation syringe is mounted in a syringe holder in a drug administration apparatus according to Embodiment 3 of the present invention.
Figure 14:
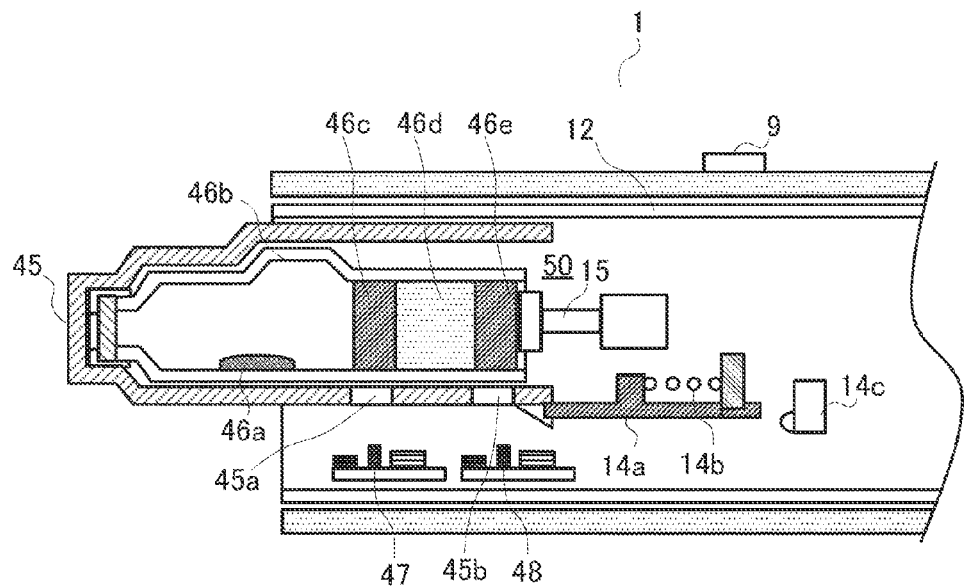
FIG. 14 is a cross sectional view showing the internal state after a formulation syringe is mounted in a syringe holder in the drug administration apparatus according to Embodiment 3.

FIG. 13 and FIG. 14 are cross sectional view showing states before and after formulation syringe 46 is mounted in drug administration apparatus 1 according to Embodiment 3 of the present invention. FIG. 13 is a cross sectional view showing the internal state before formulation syringe 46 is mounted in syringe holder 50. FIG. 14 is a cross sectional view showing the internal state after formulation syringe 46 is mounted in syringe holder 50. The same components as in FIG. 4 and FIG. 5 are assigned the same reference numerals, and overlapping descriptions will be omitted.

As shown in FIG. 13 and FIG. 14, drug administration apparatus 1 has first color detecting section 47 and second color detecting section 48. First color detecting section 47 and second color detecting section 48 will be described later with reference to FIG. 15. Providing two color detecting sections, first color detecting section 47 and second color detecting section 48, allows color detection in a plurality of positions and also allows more advanced automatic identification of formulation.

Syringe cover 45 has first opening 45a and second opening 45b.

Formulation syringe 46 is used by dissolving drug, and has powder formulation 46a, syringe convex part 46b, first basket 46c, drug solution 46d and second gasket 46e.

FIG. 13 shows a state before syringe cover 45 is mounted, where syringe cover 45 is removed from drug administration apparatus 1, and, after formulation syringe 46 is inserted in drug administration apparatus 1, syringe cover 45 is mounted, and then fitted into piston case 12 placed in housing 2.

FIG. 14 shows a state after syringe cover is mounted.

Figure 15:
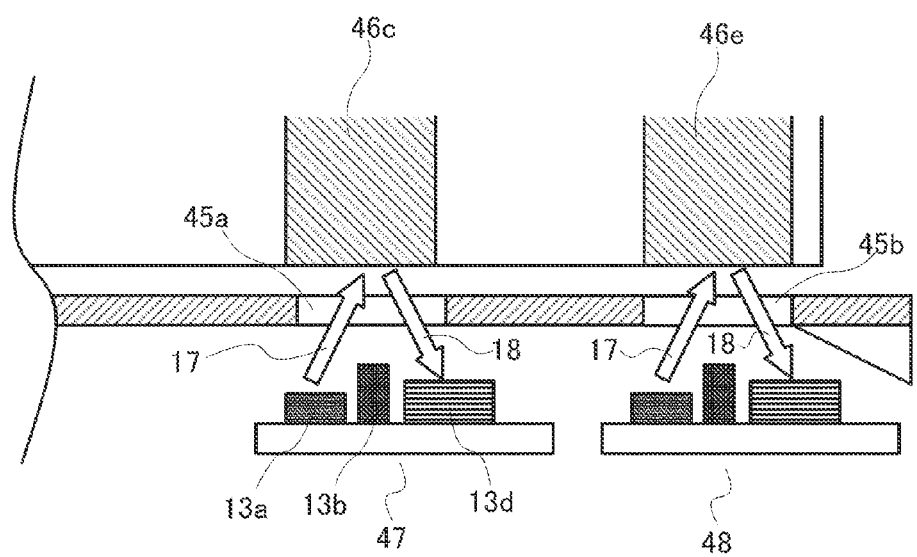
FIG. 15 is an enlarged cross sectional view showing primary parts nearby a first color detecting section and a second color detecting section in the drug administration apparatus according to Embodiment 3.

FIG. 15 is an enlarged cross sectional view showing primary parts nearby the above-described first color detecting section 47 and second color detecting section 48. The same components as in FIG. 6 are assigned the same reference numerals, and overlapping descriptions will be omitted.

First color detecting section 47 and second color detecting section 48 have the same configuration as color detecting section 13 shown in FIG. 6. Color detecting sections 13 shown in FIG. 6 are provided in two positions as first color detecting section 47 and second color detecting section 48.

When white light 17 containing RGB components outputted from LED 13a hits first gasket 46c and second gasket 46e, white light 17 is converted into reflected lights 18 respectively having the same color components as gaskets (46c and 46E). First color detecting section 47 and second color detecting section 48 perform digital-conversion on each reflected light 18 and outputs the result to microprocessor 20 to accomplish color detection.

Figure 16:
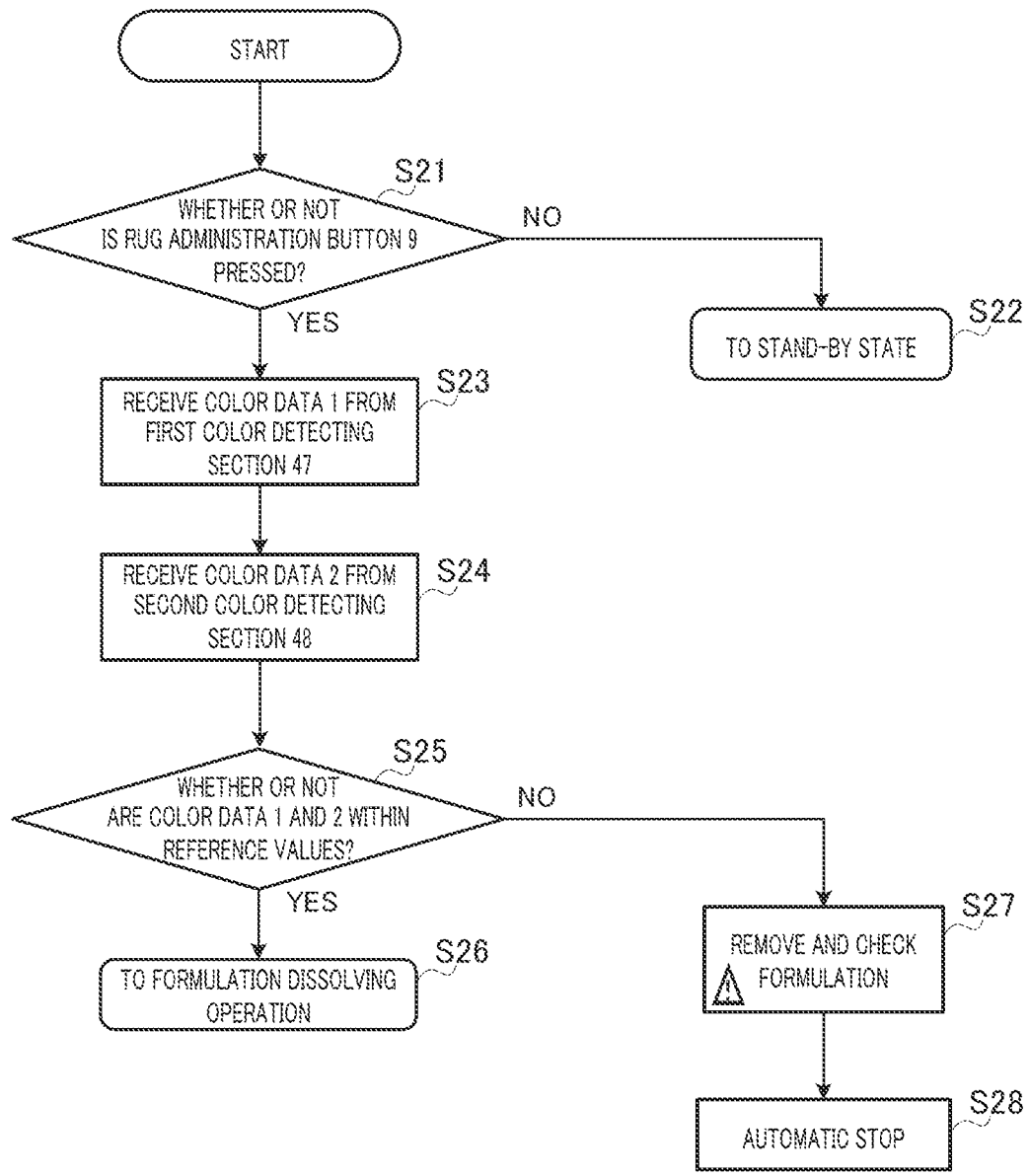
FIG. 16 is a flowchart showing operation of formulation identification when a formulation syringe is replaced in the drug administration apparatus according to Embodiment 1.

FIG. 16 is a flowchart showing operation of formulation identification at the time of replacing formulation syringe 46 (used by dissolving drug).

In step S21, microprocessor 20 checks whether or not drug administration button 9 has been pressed by the user. If drug administration button 9 has not been pressed by the user, the step moves to a stand-by mode in step S22.

On the other hand, if drug administration button 9 has been pressed by the user, the step moves to step S23, and microprocessor 20 receives color data 1 from first color detecting section 47, and next, receives color data 2 from second color detecting section 48 in step S24.

In step S25, microprocessor 20 determines whether or not color data 1 and color data 2 received from first color detecting section 47 and second color detecting section 48 are within reference values, respectively.

If color data 1 and color data 2 are within the reference values, microprocessor 20 determines that inserted formulation syringe 46 is new, and moves to step S26.

In step S26, microprocessor 20 drives piston driving motor 16 incorporated in drug administration apparatus 1 to move piston 15 forward a certain distance, so that formulation automatically dissolve.

If color data 1 and color data 2 are out of the reference values in the above step S25, the step moves to step S27.

In step S27, microprocessor 20 issues a message indicating that formulation should be checked. To be more specific, in order to report to the user that wrong drug is likely to be administrated, microprocessor 20 displays a caution or warning as a message indicating "! remove and check formulation" on LCD 10, which is a display means. In addition, microprocessor 20 makes sounder 25 issue a warning sound and also makes vibrator 26 vibrate. Moreover, microprocessor 20 may issue a warning by flashing a display LED. Furthermore, combination of these is possible.

In step S28, microprocessor 20 commands drug administration apparatus 1 to automatically stop in order to prevent wrong drug from being administered. Providing a drug administration preventing means for automatically preventing wrong drug from being administered in the drug administration apparatus 1 side is greatly useful to secure the safety of the user.

In this way, according to Embodiment 3, it is possible to identify the color of gaskets in a formulation syringe, and therefore it is possible to easily automatically identify the state of preservation of formulation, that is, it is determine whether or not the formulation is new.

For example, in a drug administration apparatus in which formulation is dissolved in use, it is possible to automatically dissolve formulation after the color of gaskets placed in two positions in the formulation syringe is determined. In addition, a specific effect of supporting automatic identification of various types of formulation is provided.

Embodiment 4 is an example in which two types of color detecting means, a reflective color detecting section and a transmissive color detecting section, are provided.

Figure 17:
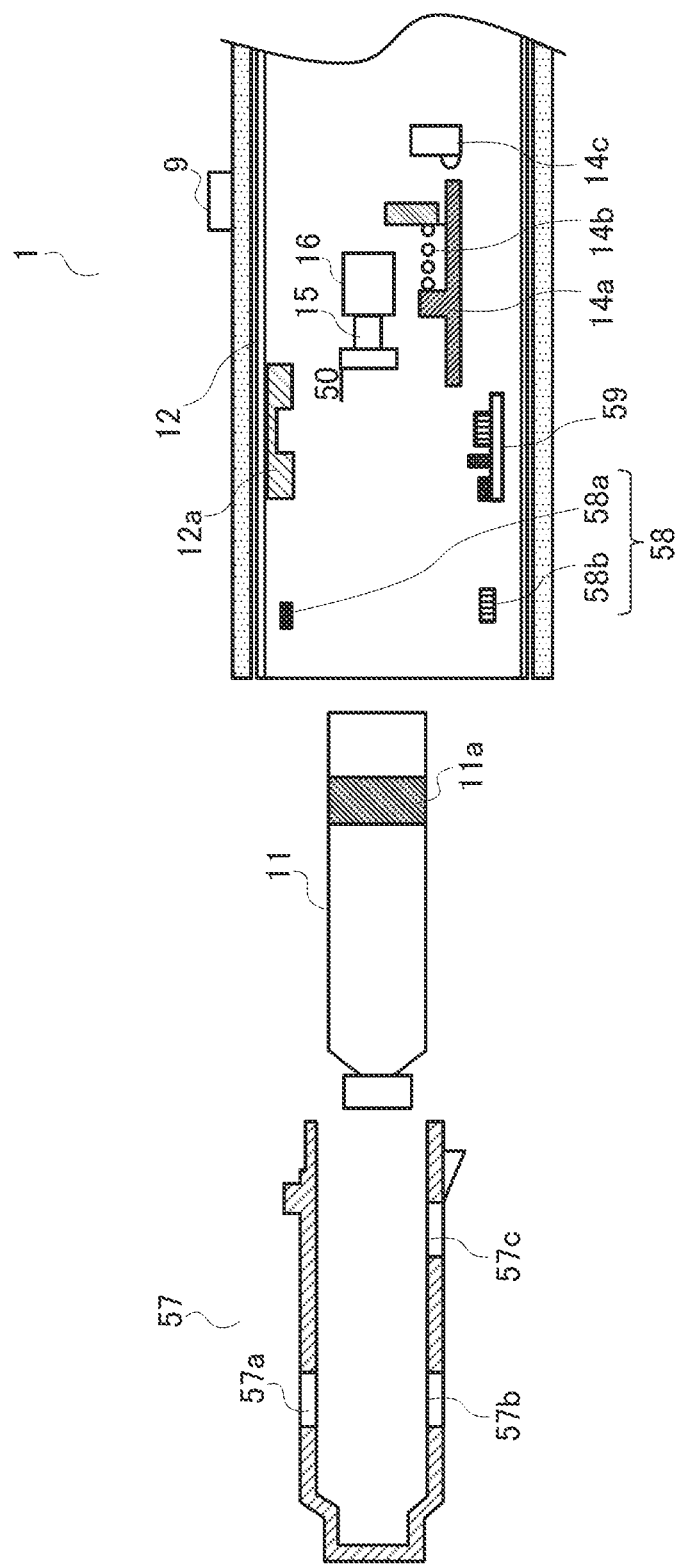
FIG. 17 is a cross sectional view showing the internal state before a formulation syringe is mounted in a syringe holder in a drug administration apparatus according to Embodiment 4 of the present invention.
Figure 18:
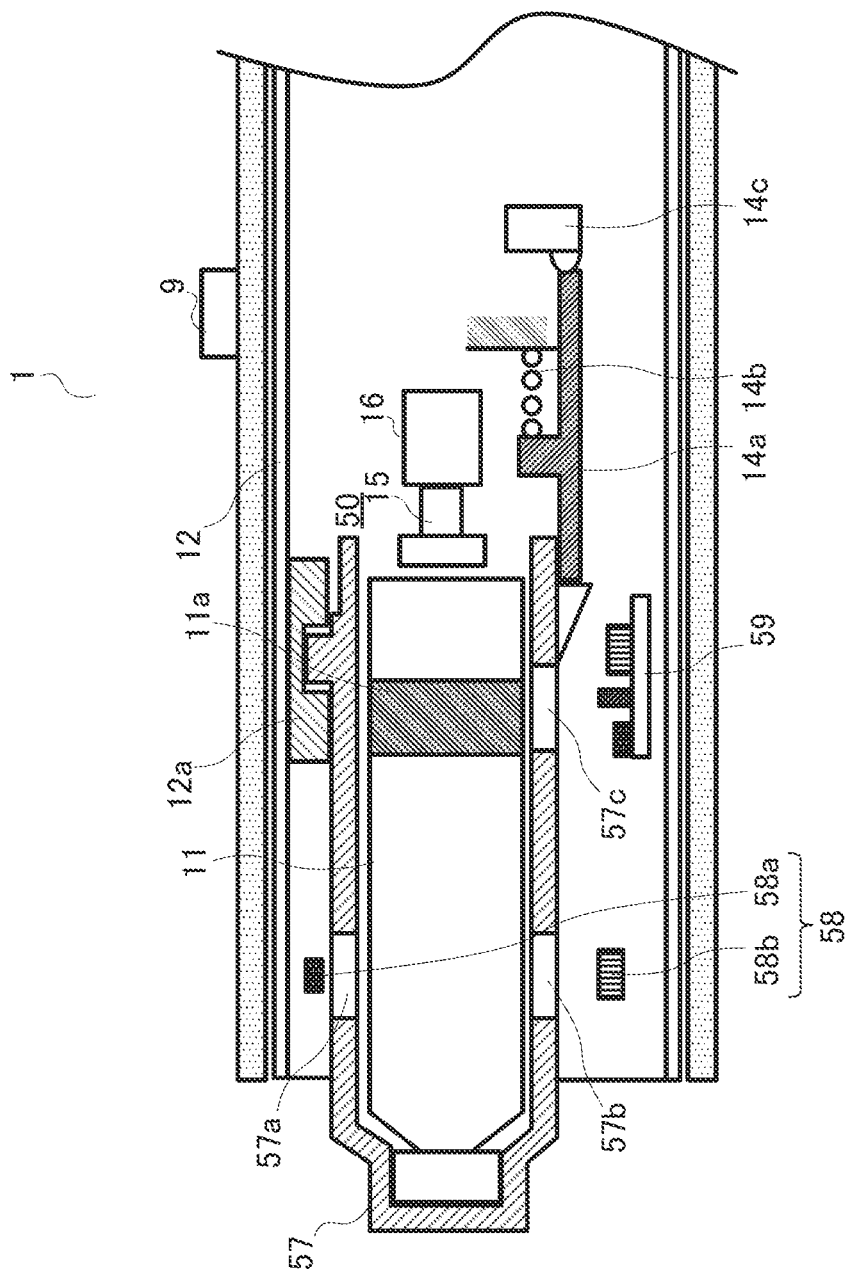
FIG. 18 is a cross sectional view showing the internal state after a formulation syringe is mounted in a syringe holder in the drug administration apparatus according to Embodiment 4.

FIG. 17 and FIG. 18 are cross sectional views showing states before and after formulation syringe 11 is mounted in drug administration apparatus 1 according to Embodiment 4 of the present invention. FIG. 17 is a cross sectional view showing the internal state before formulation syringe 11 is mounted in syringe holder 50. FIG. 18 is a cross sectional view showing the internal state after formulation syringe 11 is mounted in syringe holder 50. The same components as in FIG. 4, FIG. 5, FIG. 13 and FIG. 14 are assigned the same reference numerals, and overlapping descriptions will be omitted.

As shown in FIG. 17 and FIG. 18, syringe cover 57 is used to detect colors in a plurality of positions, and has first opening section 57a, second opening section 57b and third opening section 57c.

Formulation syringe 11 has label 11a used for color detection.

First color detecting section 58 has LED 58a and color sensor 58b, and can detect colors by performing digital-conversion on passed light from formulation syringe 11 and outputting the result to microprocessor 20, like transmissive color detecting section 43 shown in FIG. 12.

Second color detecting section 59 has the same configuration as color detecting section 13 shown in FIG. 6, and can detect colors by performing digital-conversion on passed light from formulation syringe 11 and outputting the result to microprocessor 20.

Providing first color detecting section 58 and second color detecting section 59 placed in two positions allows color detection in a plurality of positions, and also allows more advanced automatic identification of formulation.

Figure 19:
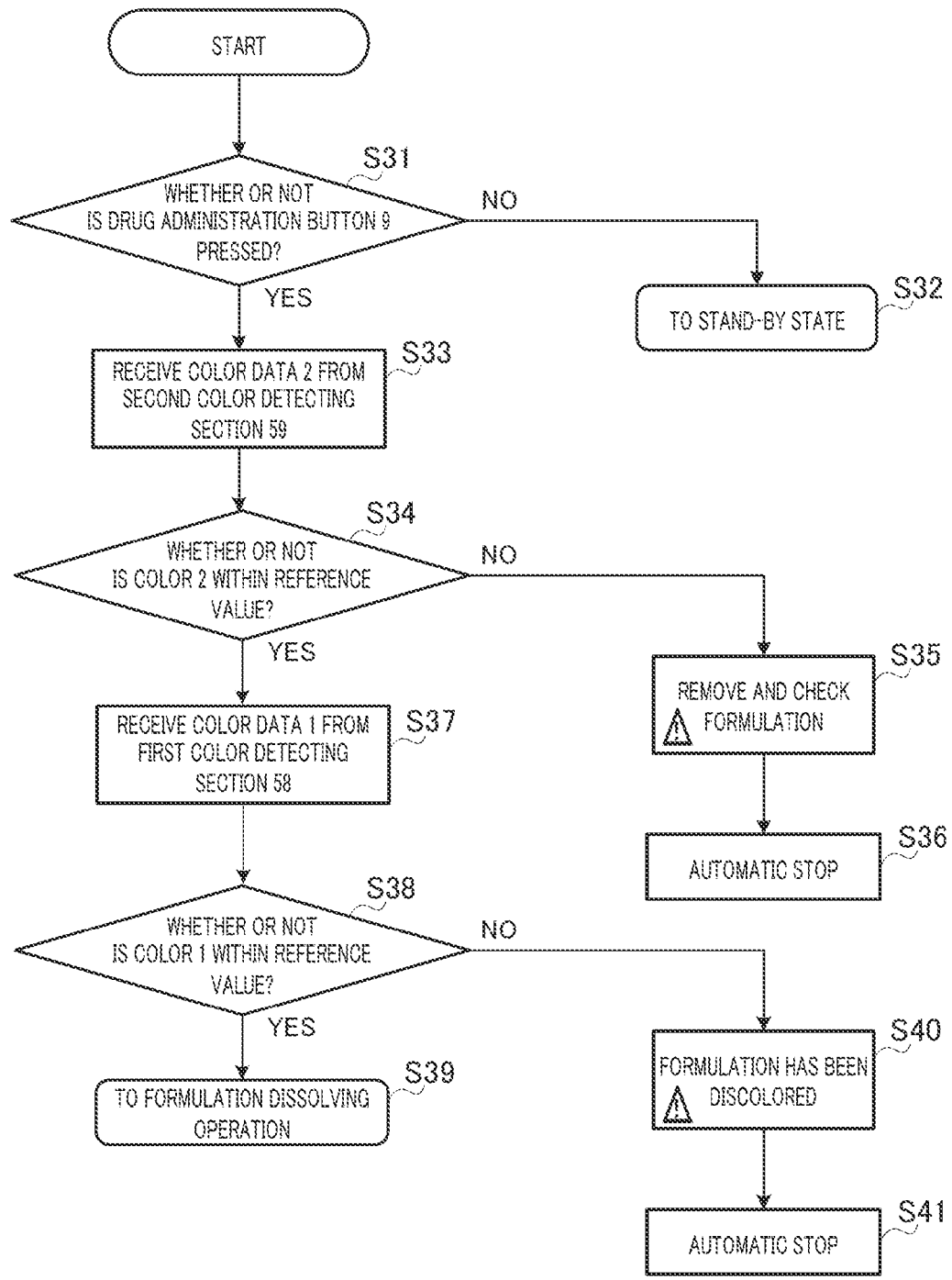
FIG. 19 is a flowchart showing operation of formulation identification using a first color detecting section and a second color detecting section in the drug administration apparatus according to Embodiment 4.

FIG. 19 is a flowchart showing operation of formulation identification using first color detecting section 58 and second color detecting section 59.

In step 31, microprocessor checks whether or not drug administration button 9 has been pressed by the user. If drug administration button 9 has not been pressed by the user, the step moves to a stand-by mode in step S32.

On the other hand, if drug administration button 9 has been pressed by the user, microprocessor 20 receives color data 2 from second color detecting section 59 in step S33.

In step S34, microprocessor 20 determines whether or not color data 2 received from second color detecting section 49 is within the reference value.

If color data 2 is out of the reference value in the above step S35, microprocessor 20 issues a message indicating that formulation should be checked. To be more specific, in order to report to the user that wrong drug is likely to be administrated, microprocessor 20 displays a caution or warning as a message indicating "! remove and check formulation" on LCD 10, which is a display means. In addition, microprocessor 20 makes sounder 25 issue a warning sound and also makes vibrator 26 vibrate. Moreover, microprocessor 20 may issue a warning by flashing a display LED. Furthermore, combination of these is possible.

In step S36, microprocessor 20 commands drug administration apparatus 1 to automatically stop in order to prevent wrong drug from being administered. Automatically preventing wrong drug from being administered in the drug administration apparatus 1 side is greatly useful to secure the safety of the user.

If color data 2 is within the reference value in the above step S34, microprocessor 20 receives color data 1 from first color detecting section 58 in step S37.

In step S38, microprocessor 20 determines whether or not color data 1 received from first color detecting section 58 is within the reference value.

If color data 1 is within the reference value, microprocessor 20 determines that inserted formulation syringe 11 is new, and moves to step S39.

In step S39, microprocessor 20 moves to drug administration processing.

If color data 1 is out of the reference value in the above step 38, microprocessor 20 issues a message indicating that formulation should be checked in step S40. To be more specific, in order to report to the user that deteriorated or defective drug is likely to be administrated, microprocessor 20 displays a caution or warning as a message indicating "! formulation has been discolored" on LCD 10. In addition, microprocessor 20 makes sounder 25 issue a warning sound and also makes vibrator 26 vibrate. In addition, microprocessor 20 may issue a warning by flashing a display LED. Moreover, combination of these is possible.

In step S41, microprocessor 20 makes drug administration apparatus 1 automatically stop in order to prevent deteriorated or defective drug from being administered. Providing a drug administration preventing means that prevents deteriorated or defective drug from being automatically administered in the drug administration apparatus 1 side is greatly useful to secure the safety of the user.

In this way, according to Embodiment 4, firstly, second color detecting section 59 detects the color of label 11a affixed to formulation syringe 11 to automatically identify the type of formulation syringe 11. Secondly, first color detecting section 58 detects the color of the formulation itself to automatically determine whether or not the formulation has been discolored. These two kinds of color detection are performed, so that the user does not need work including checking a formulation syringe by the user's eyes, and therefore can identify a formulation without trouble. That is, by performing color detection on the above-described two items, the user can easily and reliably identify a formulation syringe without damaging convenience for the user, and it is possible to use the drug administration apparatus more safely and improve operability.

Moreover, a case is possible where first color detecting section 58 is substituted for a reflective color detecting section as shown in Embodiment 1, and, for example, (1) irreversible temperature control indicators manufactured by Nichiyu Giken Kogyo Co., Ltd. or (2) humidity indicators such as "HumiJudge™" manufactured by Kyodo Printing Co., Ltd are arranged in predetermined positions, so that it is possible to detect the colors, or change in the colors of the temperature control indicators or the humidity indicators. An advantage is found that these color detections are applicable to a drug administration apparatus required to automatically identify more accurately the preservation state of formulation (the temperature and humidity around formulation). There color detections are expected to be widely used in various drug administration apparatuses.

The above description is illustration of preferred embodiments of the present invention and the scope of the invention is not limited to this.

Although the name "drug administration apparatus" is used in the embodiments for ease of explanation, "drug injecting device", "drug administration system" and so forth are possible naturally.

Moreover, the type, the number, the connection method and so forth of components constituting the above-described drug administration apparatus are not limited.

The above-described drug administration method may be realized by a program to operate this drug administration method. This program is stored in a computer-readable storage medium.

The disclosure of Japanese Patent Application No. 2008-320056, filed on Dec. 16, 2008, including the specification, drawings and abstract, is incorporated herein by reference in its entirety.

INDUSTRIAL APPLICABILITY

The drug administration apparatus according to the present invention is useful as a drug administration apparatus that has a function to automatically and correctly identify a formulation syringe by performing operation required for drug administration, has a formulation syringe containing formulation mounted inside, and can administer drug to a living body and so forth. Particularly, it is useful for injection into elderly people, children and physically-challenged people by themselves, injection into patients by their families, and so forth.

REFERENCE SIGNS LIST

1 Drug administration apparatus
2 Housing
3 Tip cap
4 Check window
5, 41, 45, 57 Syringe cover
5a Attaching and removing protrusion
5b Detecting protrusion
5c Opening
6 Power supply button
8 Completion button
7 Air-bleeding button
8 Completion button
9 Drug administration button
10 LCD
11, 42, 46 Formulation syringe
11a Label
12 Piston case
12a Attaching and removing groove
13 Color detecting section
13a, 43a 58a LED
13b Light blocking wall
13c, 43b, 58b Color sensor
13d Printed substrate
14 Syringe cover detecting section
14a Syringe cover detecting lever
14b Syringe cover detecting lever spring
14c Syringe cover detecting switch
15 Piston
16 Piston driving motor 19 Power supply section
19a Rechargeable battery
19b Charging circuit
20 Microprocessor
21 Motor drive circuit
22 Current detecting circuit
23 Encoder
24 Display section
25 Sounder
26 Vibrator
41a, 45a, 57a First opening
41b, 45b, 57b Second opening
42a Formulation
42b, 46c First gasket
42c, 46e Second gasket
42d Container
43 Transmissive color detecting section
46a Powder formulation
46d Drug solution
47, 58 First color detecting section
48, 59 Second color detecting section
50 Syringe holder
57c Third opening

The invention claimed is:

1. A drug administration apparatus that has a formulation syringe containing formulation mounted inside and administers drug to a living body, the drug administration apparatus comprising:
   a housing having a mounting section;
   a syringe cover configured to cover the formulation syringe;
   a syringe cover detecting section that is configured to detect the syringe cover being mounted in the mounting section, the syringe cover detecting section including a syringe cover detecting switch;
   an identification section having a color detecting section that identifies formulation loaded in the formulation syringe, or the formulation syringe containing the formulation, the formulation syringe being covered with the syringe cover; and
   a reporting section that reports a result of identification by the identification section, wherein
   the color detecting section is configured to detect at least one or more of a color of the formulation, a color of the formulation syringe, a color of a cap provided in a tip of the formulation syringe, a color of a gasket in the formulation syringe and a color of a label affixed to the formulation syringe, when or after the syringe cover detecting section detects that the syringe cover was mounted in the mounting section by the syringe cover detecting switch, and
   the identification section is configured to determine whether a color data of the color detected with the color detecting section is within a reference value.

2. The drug administration apparatus according to claim 1, wherein the color detecting section detects a color by detecting passed light passing through the formulation.

3. The drug administration apparatus according to claim 2, wherein the syringe cover has a window part, an opening or a transparent member that passes through the passed light when the formulation syringe is mounted in the drug administration apparatus.

4. The drug administration apparatus according to claim 1, wherein:
   the syringe cover has a window part, an opening or a transparent member; and
   the color detecting section detects a color through the window part, the opening or the transparent member in the syringe cover.

5. The drug administration apparatus according to claim 1, wherein the identification section has a plurality of color detecting sections that identify colors of a plurality of objects to be identified, respectively.

6. The drug administration apparatus according to claim 1, wherein the reporting section displays the result of the identification.

7. The drug administration apparatus according to claim 1, wherein the reporting section reports the result of the identification by an auditory means.

8. The drug administration apparatus according to claim 1, further comprising:
   a drug administration section that performs drug administration; and
   a drug administration preventing section that stops the drug administration when the identification section determines that the formulation syringe mounted in the drug administration apparatus is not applicable.

9. The drug administration apparatus according to claim 1, further comprising a formulation replacement detecting section,
   wherein the identification section performs the identification when the formulation replacement detecting section detects the formulation syringe being replaced.

10. The drug administration apparatus according to claim 1, further comprising a drug administration section that performs drug administration,
    wherein the identification section performs the identification when the drug administration section starts drug administration.

11. The drug administration apparatus according to claim 1,
    wherein the identification section performs the identification when or after the formulation syringe is mounted in the mounting part and also performs the identification when the drug administration starts.

12. The drug administration apparatus according to claim 1, further comprising a formulation syringe detecting section that detects the formulation or the formulation syringe being mounted in a drug administration apparatus body.

13. The drug administration apparatus according to claim 1, further comprising a drug dosage control section that automatically administers a predetermined dosage of drug from the formulation syringe into a living body, according to information about the predetermined dosage of drug set in advance.

14. The drug administration apparatus according to claim 13, further comprising a drug administration information setting section that can set in advance information about a dosage of drug to be administered to the living body.

15. The drug administration apparatus according to claim 1, wherein the identification section has a color detecting section that determines that the formulation or the formulation syringe is new.

16. A drug administration apparatus that has a formulation syringe containing formulation mounted inside and administers drug to a living body, the drug administration apparatus comprising:
    a housing having a mounting section;
    a syringe cover configured to cover the formulation syringe;
    a syringe cover detecting section that is configured to detect the syringe cover being mounted in the mounting section, the syringe cover detecting section including a syringe cover detecting switch;

an identification section having a color detecting section that identifies formulation loaded in the formulation syringe, or the formulation syringe containing the formulation; and a reporting section that reports a result of identification by the identification section, wherein the formulation syringe is integrally formed with the syringe cover which is configured to be mounted in the drug administration apparatus; and the color detecting section is configured to detect a color of the syringe cover or the color of the label affixed to the syringe cover, when or after the syringe cover detecting section detects that the syringe cover was mounted in the mounting section by the syringe cover detecting switch, and the identification section is configured to determine whether a color data of the color detected with the color detecting section is within a reference value.

17. The drug administration apparatus according to claim 16, wherein the identification section has a plurality of color detecting sections that identify colors of a plurality of objects to be identified, respectively.

18. The drug administration apparatus according to claim 16, further comprising:

a drug administration section that performs drug administration; and a drug administration preventing section that stops the drug administration when the identification section determines that the formulation syringe mounted in the drug administration apparatus is not applicable.

19. The drug administration apparatus according to claim 16, further comprising a formulation replacement detecting section, wherein the identification section performs the identification when the formulation replacement detecting section detects the formulation syringe being replaced.

20. The drug administration apparatus according to claim 16, further comprising a drug dosage control section that automatically administers a predetermined dosage of drug from the formulation syringe into a living body, according to information about the predetermined dosage of drug set in advance.

21. The drug administration apparatus according to claim 20, further comprising a drug administration information setting section that can set in advance information about a dosage of drug to be administered to the living body.

22. The drug administration apparatus according to claim 16, wherein the identification section has a color detecting section that determines that the formulation or the formulation syringe is new.

* * * * *

UNITED STATES PATENT AND TRADEMARK OFFICE
CERTIFICATE OF CORRECTION

PATENT NO.        : 8,771,233 B2
APPLICATION NO.   : 13/133229
DATED             : July 8, 2014
INVENTOR(S)       : Atsushi Watanabe, Seiji Kikuchi and Tsuguhiro Kondo It is certified that error appears in the above-identified patent and that said Letters Patent is hereby corrected as shown below:

On the Title page, after the listing of the inventors, please insert item --(73) Assignee: Panasonic Healthcare Co., Ltd., Ehime (JP)--

Signed and Sealed this
Eleventh Day of August, 2015

Michelle K. Lee
*Director of the United States Patent and Trademark Office*